(12) United States Patent
Jain et al.

(10) Patent No.: US 10,400,594 B2
(45) Date of Patent: Sep. 3, 2019

(54) PETROPHYSICAL RELATIONSHIPS USING BLIND SOURCE SEPARATION TECHNIQUES

(71) Applicant: Schlumberger Technology Corporation, Sugar Land, TX (US)

(72) Inventors: Vikas Jain, Sugar Land, TX (US); Kais Gzara, Tunis (TN); Chanh Cao Minh, Katy, TX (US); Roger Griffiths, Selangor (MY)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 479 days.

(21) Appl. No.: 14/971,117

(22) Filed: Dec. 16, 2015

(65) Prior Publication Data

US 2016/0178546 A1 Jun. 23, 2016

Related U.S. Application Data

(60) Provisional application No. 62/093,374, filed on Dec. 17, 2014.

(51) Int. Cl.

| E21B 49/08 | (2006.01) |
|---|---|
| G01N 33/28 | (2006.01) |
| G01N 11/00 | (2006.01) |
| E21B 47/10 | (2012.01) |
| E21B 49/00 | (2006.01) |
| G01N 24/08 | (2006.01) |

(52) U.S. Cl.
CPC .............. *E21B 49/08* (2013.01); *E21B 47/10* (2013.01); *E21B 49/00* (2013.01); *G01N 11/00* (2013.01); *G01N 33/2823* (2013.01); *G01N 24/081* (2013.01)

(58) Field of Classification Search
CPC .. G01N 11/00; G01N 33/2823; G01N 24/081; E21B 49/08; E21B 49/00; E21B 47/10
See application file for complete search history.

(56) References Cited

U.S. PATENT DOCUMENTS

| 9,223,055 | B2 | 12/2015 | Jain et al. | |
|---|---|---|---|---|
| 2003/0231017 | A1* | 12/2003 | Kiesl | E21B 33/1243 324/303 |
| 2011/0068788 | A1* | 3/2011 | Minh | G01V 3/18 324/303 |
| 2013/0110486 | A1* | 5/2013 | Polyakov | E21B 49/00 703/10 |
| 2013/0200891 | A1* | 8/2013 | Kruspe | G01N 24/081 324/303 |
| 2013/0268201 | A1 | 10/2013 | Gzara et al. | |
| 2014/0129149 | A1 | 5/2014 | Gzara et al. | |
| 2015/0015250 | A1 | 1/2015 | Gzara et al. | |
| 2017/0111112 | A1* | 4/2017 | San Martin | H04B 10/0795 |

\* cited by examiner

*Primary Examiner* — Ajay Ojha

(57) ABSTRACT

A method for generating a model of a formation property includes acquiring a formation property measurement. A petrophysical quantity is inverted from the formation property measurement. A model is generated based on the inverted petrophysical quantity.

20 Claims, 10 Drawing Sheets

PETROPHYSICAL RELATIONSHIPS USING BLIND SOURCE SEPARATION TECHNIQUES

CROSS-REFERENCE TO RELATED APPLICATIONS

This application claims the benefit of a related U.S. Provisional Patent Application having Ser. No. 62/093,374, filed Dec. 17, 2014, titled "Creating Data-Driven Petrophysical Relationships Using Blind Source Separation Techniques," to Vikas Jain et al., the disclosure of which is incorporated by reference herein in its entirety.

FIELD

This disclosure relates to the measurements of formation parameters at a well-site or at subsurface locations.

BACKGROUND

A downhole tool may include a logging-while-drilling ("LWD") tool and a measurement-while-drilling ("MWD") tool. The LWD tool may be configured to measure one or more formation properties and/or physical properties as the wellbore is being drilled or at any time thereafter. The MWD tool may be configured to measure one or more physical properties as the wellbore is being drilled or at any time thereafter. The formation properties may include resistivity, density, porosity, sonic velocity, gamma rays, and the like. The physical properties may include pressure, temperature, wellbore caliper, wellbore trajectory, a weight-on-bit, torque-on-bit, vibration, shock, stick slip, and the like. The measurements from the LWD tool may be sent to the MWD tool. The MWD tool may then group the sets of data from the LWD tool and the MWD tool and prepare the data for transmission to the surface after proper encoding.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method for generating a model of a formation property is disclosed. The method includes acquiring a formation property measurement. A petrophysical quantity is inverted from the formation property measurement. A model is generated based on the inverted petrophysical quantity.

A method for determining a viscosity of a fluid in a subterranean formation is also disclosed. The method includes measuring a nuclear magnetic resonance T2 distribution of fluids in a wellbore using a downhole tool. The fluids includes oil, gas, and water. A temperature while drilling of the fluids is measured using the downhole tool. A pressure while drilling of the fluids is also measured using the downhole tool. A viscosity of the fluids is determined from the nuclear magnetic resonance T2 distribution, the temperature, and the pressure.

A computing system is also disclosed. The computing system includes a processor and a memory system including a non-transitory computer-readable medium storing instructions that, when executed by the processor, causes the computing system to perform operations. The operations include acquiring a measurement related to a formation property. The operations also include inverting a petrophysical quantity from the acquired measurement. The operations further include generating a model of the formation property based on the inverted petrophysical quantity.

Other aspects and advantages of the claimed subject matter will be apparent from the following description and the appended claims.

DETAILED DESCRIPTION

One or more specific embodiments of the present disclosure are described below. These embodiments are merely examples of the presently disclosed techniques. Additionally, in an effort to provide a concise description of these embodiments, all features of an actual implementation may not be described in the specification. It should be appreciated that in the development of any such implementation, as in any engineering or design project, numerous implementation-specific decisions are made to achieve the developers' specific goals, such as compliance with system-related and business-related constraints, which may vary from one implementation to another. Moreover, it should be appreciated that such development efforts might be complex and time consuming, but would nonetheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The embodiments discussed below are intended to be examples that are illustrative in nature and should not be construed to mean that the specific embodiments described herein are necessarily preferential in nature. Additionally, it should be understood that references to "one embodiment" or "an embodiment" within the present disclosure are not to be interpreted as excluding the existence of additional embodiments that also incorporate the recited features.

Logging measurements acquired in a wellbore may be affected by an underlying petrophysical system which may be at a different state at the time or depth of a specific measurement. A user may be unaware of the number and values of variables that make up the underlying petrophysical system. However, measurements may be related to one another because they are measuring the same latent variables. Thus, any methods of finding these relationships may help unravel the underlying system and corresponding latent variables affecting the acquired measurements.

The systems and methods disclosed herein may generalize and extend the above-mentioned work by using blind source separation techniques to unravel the hidden relationships between different types of measurements acquired at the same time or different times and/or at the same depth or different depths. As used herein, "blind source separation" refers to the separation of a set of source signals from a set of mixed signals, without the aid of information (or with very little information) about the source signals or the mixing process. In general, the number of source signals (e.g., petrophysical variables) may be less than the number of mixed signals (e.g., logging measurements).

Figure 1:
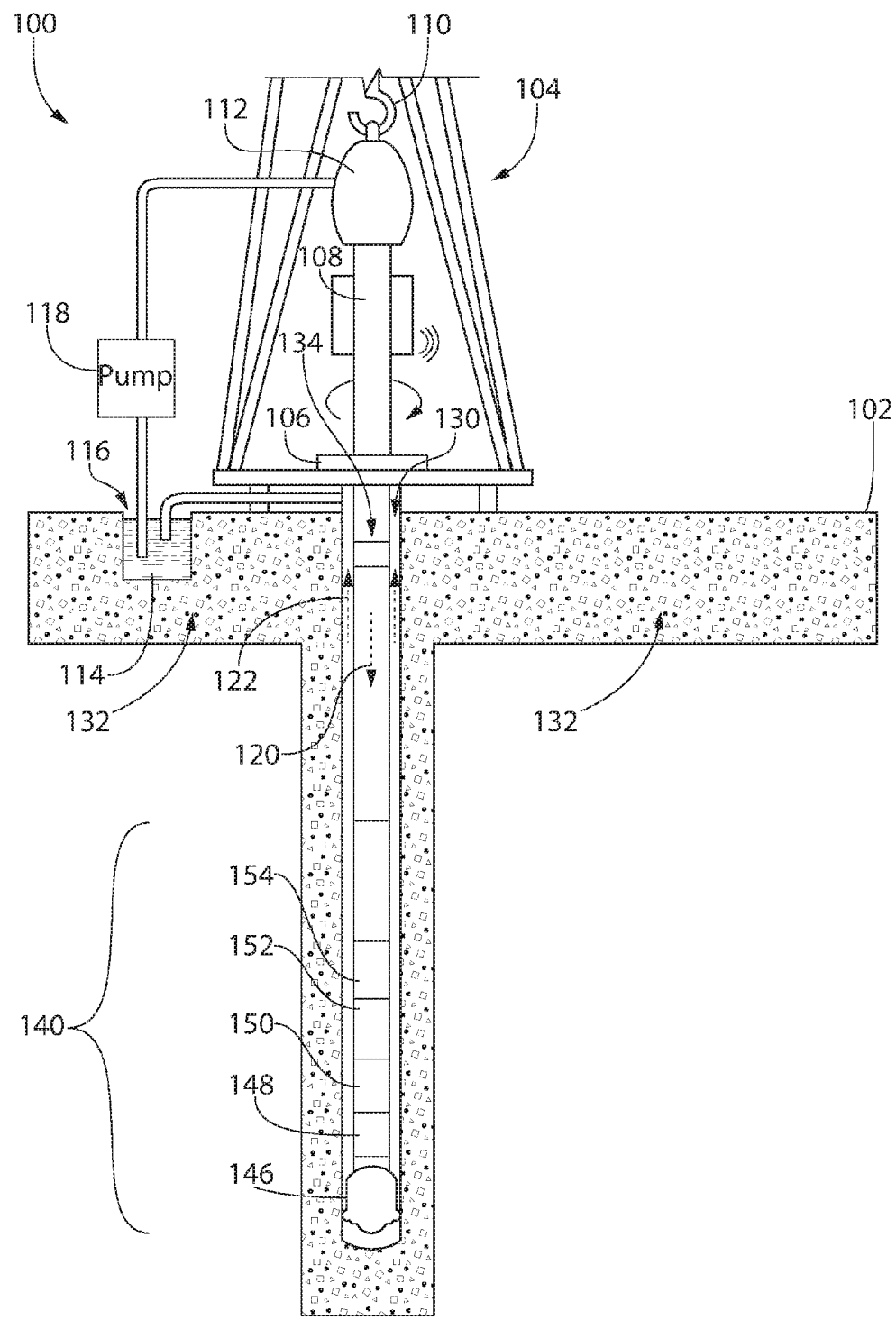
FIG. 1 illustrates a cross-sectional view of a wellsite system including a downhole tool positioned in a wellbore, according to an embodiment.

FIG. 1 illustrates a cross-sectional view of a wellsite system 100 including a downhole tool 140 positioned in a wellbore 130, according to an embodiment. The wellbore 130 may be formed in a subsurface formation 132 by rotary drilling in a manner that is well known to those skilled in the art. Some embodiments may also use directional drilling.

The well site system 100 may include a platform and derrick assembly 104 positioned over the wellbore 130, with the derrick assembly 104 including a rotary table 106, a kelly 108, a hook 110, and a rotary swivel 112. In a drilling operation, a drill string 134 may be rotated by the rotary table 106, which engages the kelly 108 at the upper end of the drill string 134. The drill string 134 may be suspended from the hook 110, attached to a traveling block (not shown), through the kelly 108 and the rotary swivel 112, which permits rotation of the drill string 134 relative to the hook 110.

Drilling fluid or mud 114 may be stored in a pit 116 formed at the well site. A pump 118 may deliver the drilling fluid 114 to the interior of the drill string 134 via a port in the swivel 112, which causes the drilling fluid 114 to flow downwardly through the drill string 134, as indicated by the directional arrow 120. The drilling fluid exits the drill string 134 via ports in a drill bit 146, and then circulates upwardly through the annulus region between the outside of the drill string 134 and the wall of the wellbore 130, as indicated by the directional arrows 122. In this known manner, the drilling fluid lubricates the drill bit 146 and carries formation cuttings up to the surface as it is returned to the pit 114 for recirculation.

In the illustrated embodiment, the downhole tool 140 may be or include a bottom hole assembly ("BHA"). The downhole tool 140 may include a drill bit 146, a rotary steerable system ("RSS") 148, and a motor 150. The downhole tool 140 may also include a logging-while-drilling ("LWD") tool 152 and a measurement-while-drilling ("MWD") tool 154. The LWD tool 152 may be configured to measure one or more formation properties and/or physical properties as the wellbore 130 is being drilled or at any time thereafter. The MWD tool 154 may be configured to measure one or more physical properties as the wellbore 130 is being drilled or at any time thereafter. The formation properties may include resistivity, density, porosity, sonic velocity, gamma rays, and the like. The physical properties may include pressure, temperature, wellbore caliper, wellbore trajectory, a weight-on-bit, torque-on-bit, vibration, shock, stick slip, and the like. The LWD tool 152 may transmit its measurements to the MWD tool 154. The MWD tool 154 may then group the sets of data from the LWD tool 152 and the MWD tool 154 and prepare the data stream for transmission to the surface location after proper encoding, as discussed in greater detail below.

The measurements of formation properties and/or physical properties may be classified into the following categories: (1) measurements called "consonant in time" which are acquired at the same time but at different depths; (2) measurements called "consonant in space" which are acquired at the same depths but at different times; and (3) more generally measurements which are neither consonant in time nor space meaning acquired at different times and depths.

Figure 2:
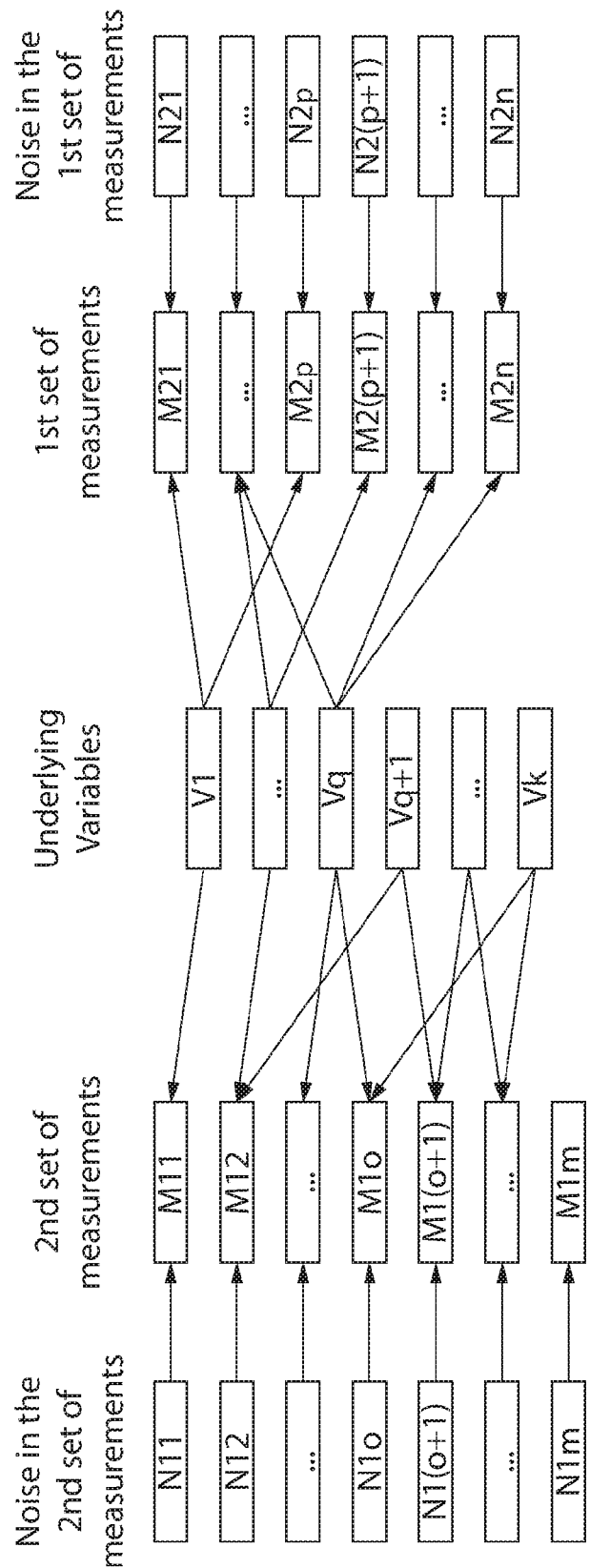
FIG. 2 illustrates a schematic view of a model representing an underlying system and acquisition of measurements, according to an embodiment.

FIG. 2 illustrates a schematic view of a model 200 representing an underlying system and acquisition of measurements, according to an embodiment. The model 200 of variables representing the underlying system and acquisition of measurements may be assumed. Two sets of measurements affected by the same underlying petrophysical system are represented by the variables V1 to Vk out of which V(q+1) to Vk are affecting the second set of measurements. $M_{ij}$ is described by i which is the set it belongs to and j which is the type of measurement it is. Thus, the two sets have some common and some different measurements as shown. Also, each measurement may have its own characteristic noise $N_{ij}$.

Measurements acquired in a single or in multiple passes may be fit into the same general model, as shown in FIG. 2. Also, the loadings of underlying variables on the measurements, shown as arrows, may be linear, piece-wise linear, or non-linear. The loading of an underlying variable, k, on a measurement, ij, is represented as $L_{ijk}$. Thus, the system of equations may be written as shown below:

$$M_{11} = \Sigma_k(L_{11k} * V_k) + N_{11} \quad (1)$$

$$M_{1m} = \Sigma_k(L_{1mk} * V_k) + N_{1m} \quad (2)$$

$$M_{21} = \Sigma_k(L_{21k} * V_k) + N_{21} \quad (3)$$

$$M_{2n} = \Sigma_k(L_{2nk} * V_k) + N_{2n} \quad (4)$$

Or, more generally in the vector form:

$$\overline{M}^i = L^i \overline{V} + \overline{N}^i \quad (5)$$

For the data acquired over depth, it may be assumed that the relative contributions of underlying variables change. Then, Equation 5 may be written in the matrix form for the depth or time based acquisition:

$$M^i = VL^i + N^i \quad (6)$$

For measurements that are not affected by a subset of underlying variables, the corresponding loadings may be set to 0. The noise in each measurement is assumed to be unique to the measurement and uncorrelated to other measurements. The same model may also be extended to more than two sets of measurements.

The variables on the right hand side of Equation 6 may be unknown. Thus, a user may either explore a single dataset using advanced data analytical techniques such as the factor analysis or understand the causes of change in two or more datasets using methods known in the art.

The user may also try to simultaneously solve multiple sets of measurements (represented by i in Equation 6). Because of the complexities involved in the method to solve such systems simultaneously, a blind source separation technique, such as, but not limited to, canonical correlation analysis ("CCA") or independent component analysis ("ICA"), may be used. Using these techniques, the user may simultaneously derive optimized basis functions for each set of measurements such that the projections of sets onto their basis axes are maximally correlated to each other. For instance, let the set of basis be $B^1$ and $B^2$ for the two set of measurements $M^1$ and $M^2$. Then, the correlation COR $(M^1B^1, M^2B^2)$ may be a diagonal matrix with decreasing correlation coefficients. Each projection may be called a canonical variate and define the set of variates $V^i$ to be:

$$V^i = M^i B^i \quad (7)$$

such that $$COR(V_p^i, V_p^j) = 0 \text{ if } p \neq q \quad (8)$$

$$COR(V_q^i, V_q^j) = [> 0.5, 1] \text{ if } p = q$$

Application 1: Petrophysical Mixing Laws

The maximum number of such canonical variates may be equal to the smallest dimension of any of the set of measurements included in the analysis. Also, correlation between corresponding variates may to be greater than about 0.5 for the applications defined below.

If there are multiple sets of the same measurements, then the canonical variates, as defined in Equation 7 and 8, may be used to determine the petrophysical mixing laws. For example, it may be assumed that there are multiple, m, apparent porosities acquired over a depth interval at different times. The time-lapse sets of m apparent porosities may be defined as $P^1$ and $P^2$. The corresponding canonical variates may be represented by $V^1$ and $V^2$. Then, $$\bar{V}_p^1 = \Sigma_m B_{pj}^1 * P_j^1 \text{ and } \bar{V}_p^2 = \Sigma_m B_{pj}^2 * P_j^2 \quad (9)$$

The correlation between the first variate may be greater than a predetermined amount. Then, from Equation 9, the true porosity $Por_{True}$ may be derived:

$$\Sigma_m B_{1j}^1 * P_j^1 = \Sigma_m B_{1j}^2 * P_j^2 = Por_{True} \quad (10)$$

Figure 3:
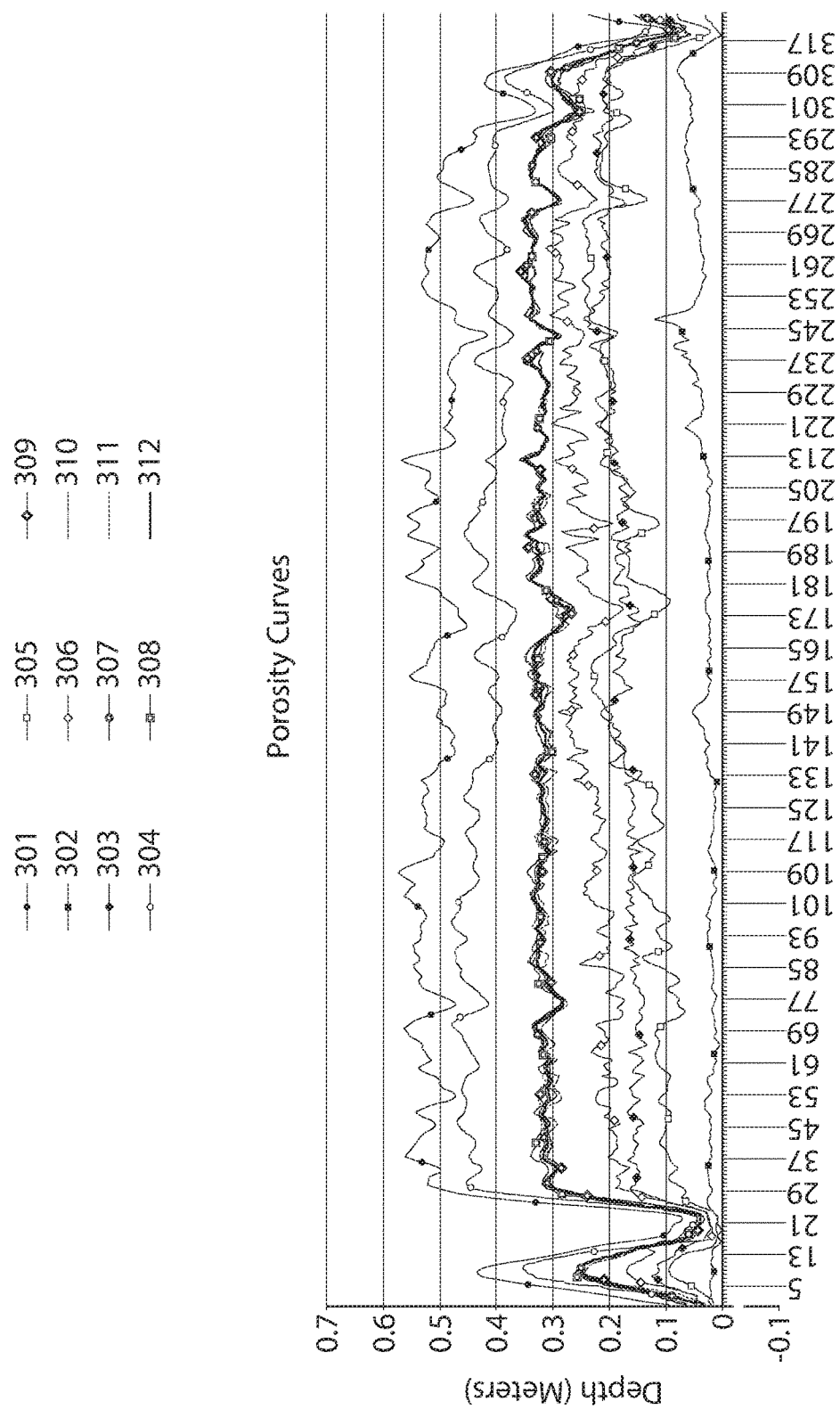
FIG. 3 illustrates a schematic view of two time-lapsed datasets, according to an embodiment.
Figure 4:
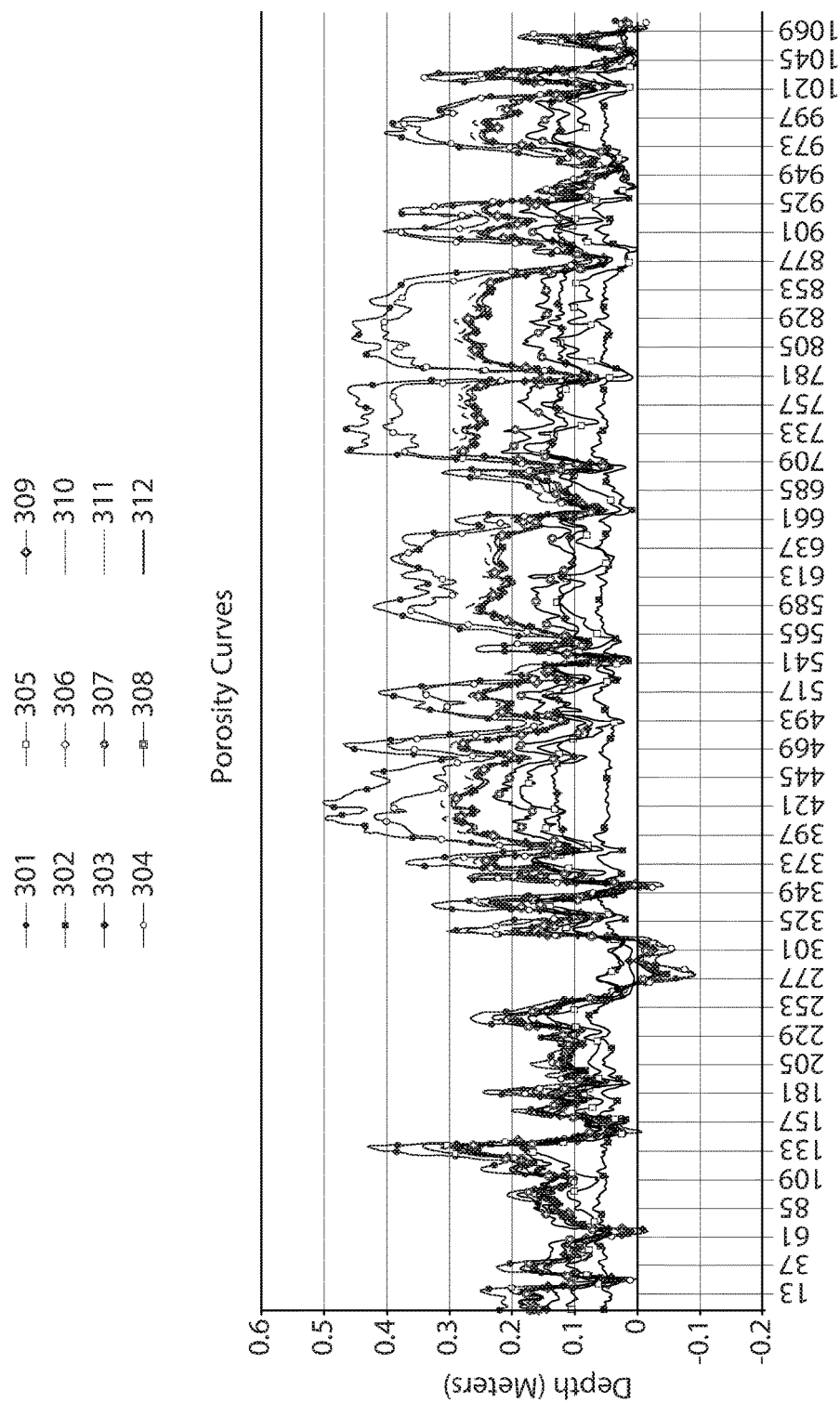
FIG. 4 illustrates another schematic view of two time-lapsed datasets, according to an embodiment.

This method described above may be applied to any set of apparent porosities with linear or non-linear relationships. FIGS. 3 and 4 each illustrate schematic graphs 300, 400 of two time-lapsed datasets, according to an embodiment. The graphs 300, 400 include a plurality of porosity curves (e.g., unitless or v/v) against depth (meters). FIG. 3 shows two time-lapse datasets that were acquired over a drill and a repeat pass. In FIGS. 3 and 4, line 301 represents the drill pass density porosity, line 302 represents the drill pass sigma porosity, line 303 represents the drill pass neutron porosity, line 304 represents the repeat pass density porosity, line 305 represents the repeat pass sigma porosity, line 306 represents the repeat pass neutron porosity, line 307 represents the true porosity (e.g., average of the porosity drill and the porosity repeat), line 308 represents the porosity drill, line 309 represents the porosity repeat, line 310 represents the canonical correlation analysis porosity drill, line 311 represents the canonical correlation analysis porosity repeat, and line 312 represents the canonical correlation analysis porosity (e.g., the average of the canonical correlation analysis porosity drill and the canonical correlation analysis porosity repeat).

The datasets include a set of apparent porosity measurements from density, sigma, and neutron measurements. Using the method described in Equations 9 and 10, the following mixing law may be determined. The average of the two is plotted as the curve 312.

$$\phi_{true} = 0.52*\phi_{drl,\rho} + 0.10*\phi_{drl,\Sigma} + 0.38*\phi_{drl,n} = 0.53*\phi_{rpt,\rho} + 0.16*\phi_{rpt,\Sigma} + 0.31*\phi_{rpt,n}$$

Application 2: Petrophysical Equation Modeling

Measurements that are made in a lab or core data may be used to establish relationships between the latent variables and acquired measurements. Once such relationships are established, then those may be applied to log-based data. For example, the viscosity of live oil is a function of NMR T2 distribution, temperature, and pressures, as shown in Equation 11.

$$\eta = f(Dist(T_2), Temp, P) \quad (11)$$

where $\eta$ is viscosity, $Dist(T_2)$ is the NMR $T_2$ distribution, Temp is temperature, and P is pressure. The $T_2$ distribution is the transverse (or "spin-spin") relaxation time.

These parameters may be measured for the available samples in a lab, and a relationship between the four variables may be determined, as shown in Equation 11. Two sets of measurements may be defined (1) $M^1$ including the $T_2$ distribution and (2) $M^2$ including the viscosity, temperature, and pressure.

$$M^1 = Dist(T_2) = [A_1, A_2, \ldots, A_c] \quad (12)$$

where A1 to Ac are the components of the T2 distribution.

$$M^2 = [\eta, Temp, P] \quad (13)$$

Using the first variates of $M^1$ and $M^2$, the user may derive a relationship such, as shown below:

$$\Sigma_c B_{1j} * A_j = B_{21} * \eta + B_{22} * Temp + B_{23} * P; \text{ or} \quad (14)$$

$$\eta = \left(\ldots B_{22} * Temp \ldots B_{23} * P + \sum_c B_{1j} * A_j\right) \Big/ B_{21} \quad (15)$$

Figure 5:
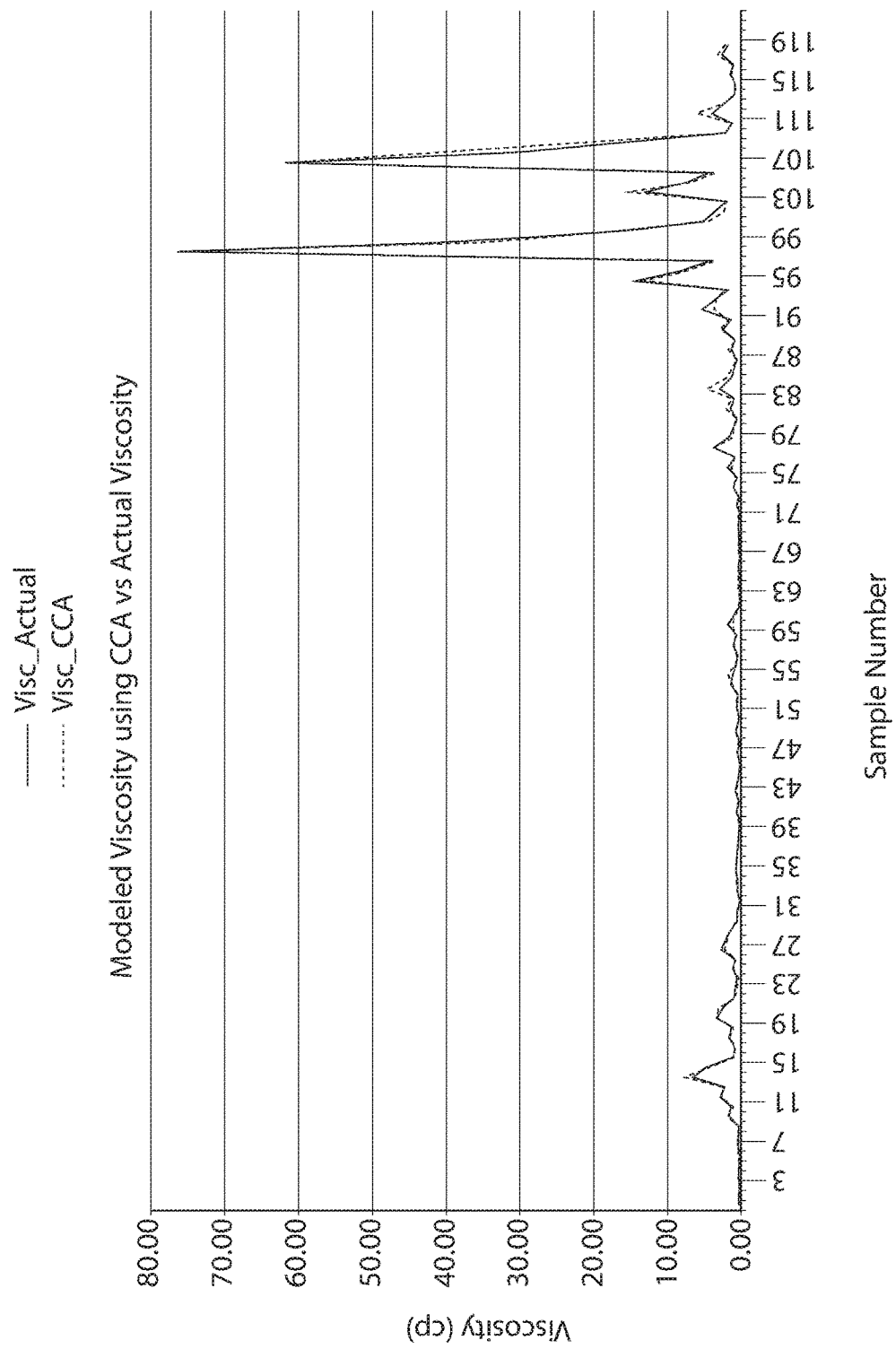
FIG. 5 illustrates a graph of modeled viscosity versus actual viscosity, according to an embodiment.

FIG. 5 illustrates a graph 500 of modeled viscosity versus actual viscosity, according to an embodiment. More particularly, FIG. 5 shows modeled viscosity using Canonical-Correlation Analysis ("CCA") versus actual viscosity. The viscosity equation is modeled using measurements made on samples. The predicted value of Visc_CCA is compared to the actual value Visc_Actual.

Application 3: Latent Variable Analysis

Canonical variates may represent the underlying latent variables. Once the nature of these latent variables is ascertained, then data-specific models may be created to help invert these latent variables.

As an example, first canonical variates called T2 Var1-2 and DGORTPVar1-2 are created using the sets of measurements of NMR T2 distributions and corresponding diffusion, gas-oil ratio, temperature, and pressure data. The variates were then found to correlate to the viscosity.

$$T_2 Var_{1-2} = \sum_i \alpha_i T_{2_i} \quad (16)$$

$$DGORTPVar_{1-2} = \sum_j \beta_j D_j + \gamma GOR + \delta T + \varepsilon P \quad (17)$$

Figure 6:
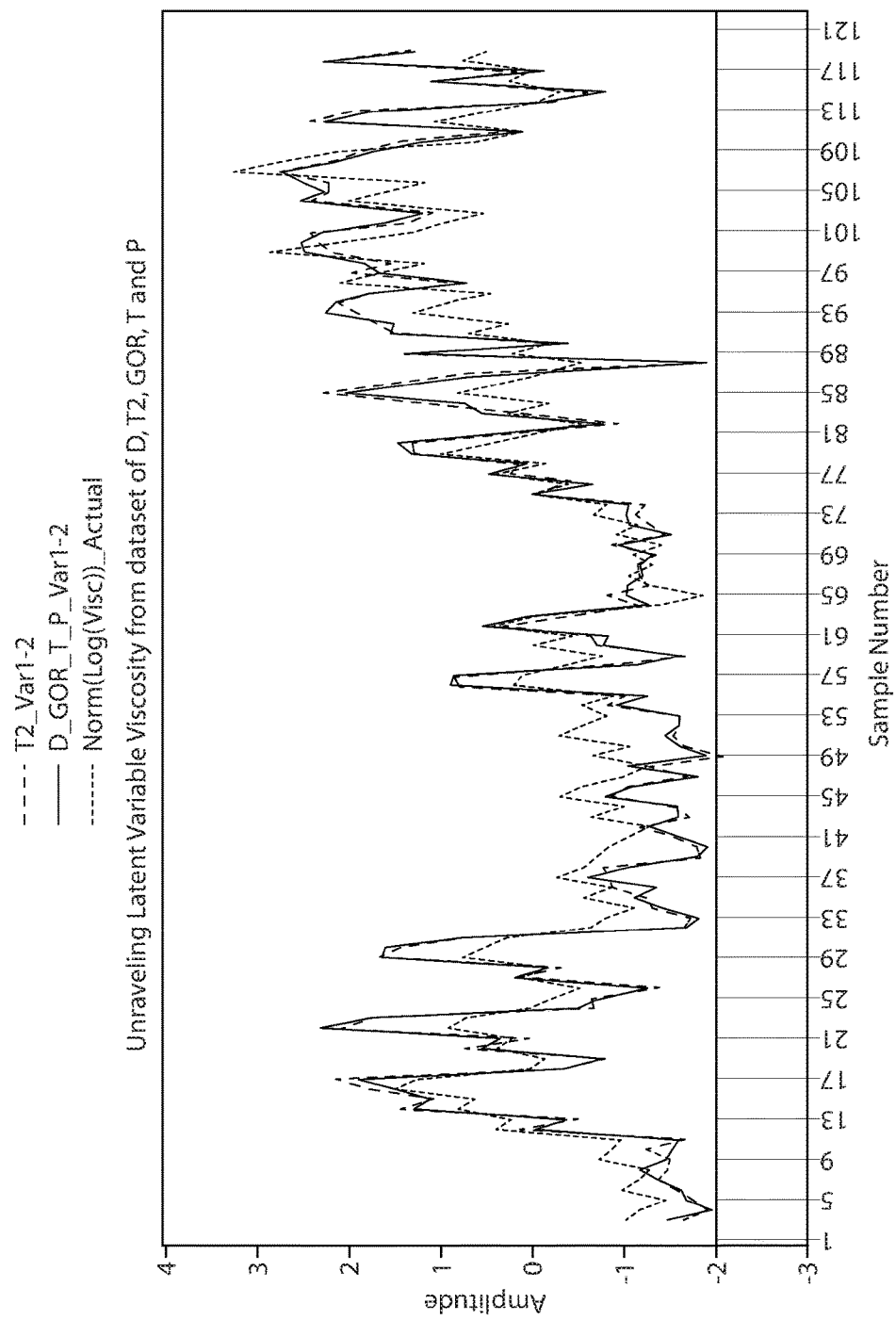
FIG. 6 illustrates a graph of unraveling latent variable viscosity from a dataset of D, T2, GOR, T and P, according to an embodiment.

FIG. 6 illustrates a graph 600 of unraveling latent variable viscosity from a dataset of D, T2, GOR, T and P, according to an embodiment. Variates may be computed using the Equations 16 and 17. The variates may then be compared to a transform of actual viscosity. Variates were found to correlate to, and represent, a latent variable, viscosity in this case.

Figure 7:
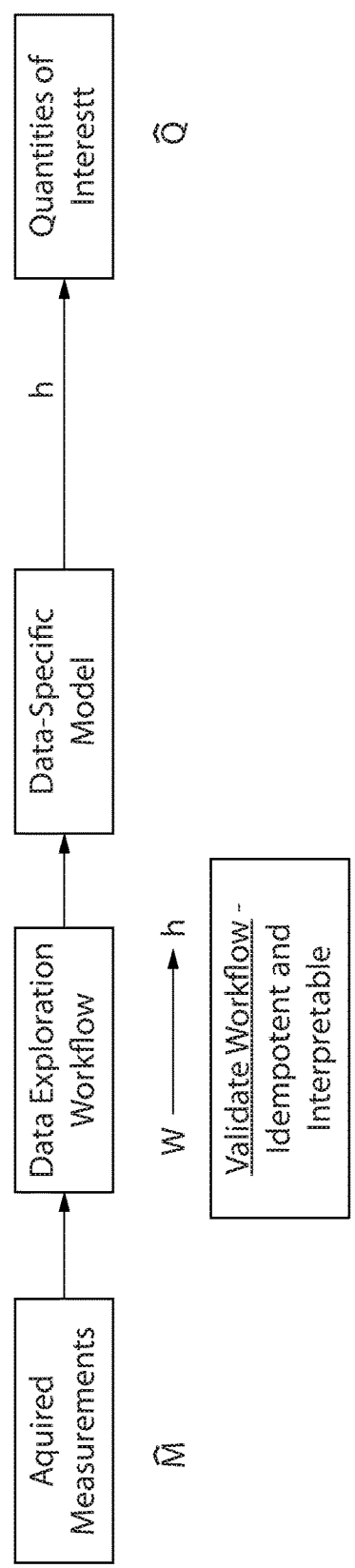
FIG. 7 illustrates a process flow diagram in accordance with embodiments described herein.

FIG. 7 illustrates a process flow diagram 700 in accordance with embodiments described herein. The process may be used to determine an underlying model using acquired measurements and using the model to derive petrophysical quantities of interest.

Figure 8:
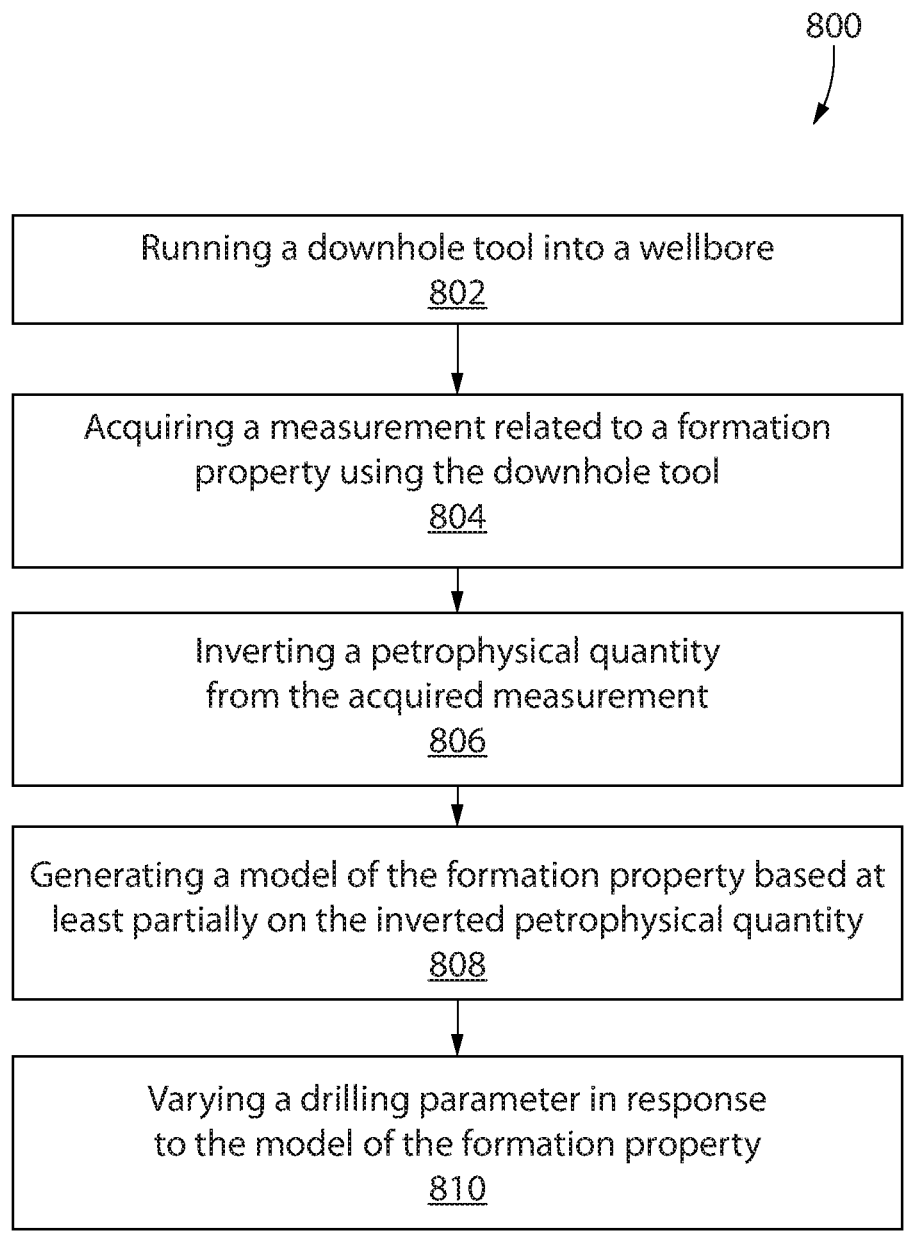
FIG. 8 illustrates a flowchart of a method for determining a model of formation properties, according to an embodiment.

FIG. 8 illustrates a flowchart of a method 800 for generating a model of formation properties, according to an embodiment. The method 800 may include running a downhole tool 140 into a wellbore 130, as at 802. The method 800 may also include acquiring one or more measurements related to formation properties and/or physical properties using the downhole tool 140 when the downhole tool 140 is in the wellbore 130, as at 804. The measurements may be acquired while drilling and/or post-drilling. The measurements may be acquired, for example, using the LWD tool 152, the MWD tool 154, or another sensor in the downhole tool 140. In another embodiment, the measurements may be acquired using a downhole tool run into the wellbore 130 on a wireline or coiled tubing (e.g., after the drill string 134 and downhole tool 140 are pulled to the surface). The measurements may be acquired in an open-hole portion of the wellbore 130 or a cased-hole portion of the wellbore 130. In at least one embodiment, the downhole tool 140 (or the downhole tool on the wireline or coiled tubing) may acquire cuttings that may be analyzed at the surface. The measurements may be or include resistivity, nuclear (e.g., density, neutron, gamma-ray, spectroscopy, capture sigma, etc.), acoustic, NMR, bulk density, or a combination thereof that are related to formation properties of, for example, porosity, mineralogy, fluid volumes, etc.

The method 800 may also include inverting one or more petrophysical quantities of interest from the acquired measurements, as at 806. The petrophysical quantities may be or include porosity, mineralogy (e.g., lithology), fluid volumes and properties (e.g., salinity, API), or a combination thereof. The inversion process is described in Equations 1-8 above.

The method 800 may also include generating or developing one or more models of the formation properties based at least partially on the inverted petrophysical quantities of interest, as at 808. One example of a model is shown in FIG. 2, which includes a porosity model. Another example of a model is shown in FIG. 3, which includes an oil viscosity model. In one embodiment, the model(s) may be generated using measurements that are sensitive to porosity (e.g., density, neutron, sonic, NMR, etc.). For example, in the development of the viscosity model shown in FIG. 3, the measurements may be sensitive to viscosity (NMR, gas/oil ratio ("GOR"), pressure, temperature, etc.) among the multiple sets of measurements.

The method 800 may also include varying one or more drilling parameters in response to the model(s) of the formation properties, as at 810. The drilling parameters may be or include a weight on the drill bit 146. For example, the weight on the drill bit 146 may be related to the formation hardness, which may be related to lithology. In at least one embodiment, a WOB petrophysical model may also be used in conjunction with the model(s) above to determine how to vary with weight on the drill bit 146.

The drilling parameters may also include a direction that the downhole tool 140 is drilling. For example, the model(s) above may be combined with knowledge of the length of the downhole tool 140 and/or the position of one or more stabilizers in the wellbore 130 to vary a direction that the downhole tool 140 drills. The drilling parameters may also include a volumetric flow rate of fluid being pumped into the wellbore 130 or properties of the fluid that is pumped into the wellbore 130.

Figure 9:
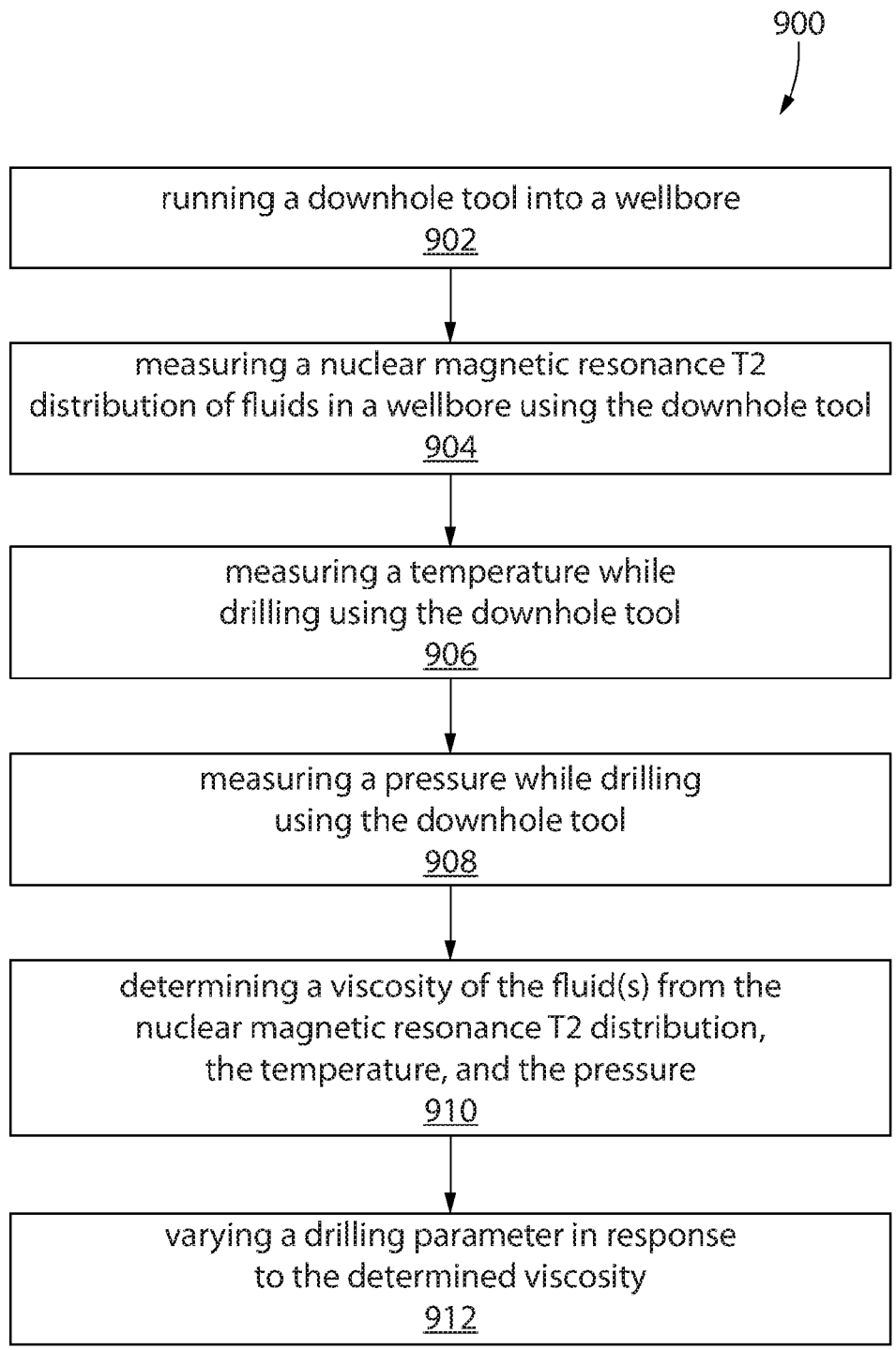
FIG. 9 illustrates a flowchart of a method for determining a viscosity, according to an embodiment.

FIG. 9 illustrates a flowchart of a method 900 for determining a viscosity of a fluid in a subterranean formation, according to an embodiment. The method 900 may include running a downhole tool 140 into a wellbore 130, as at 902. The method 900 may include measuring a nuclear magnetic resonance T2 distribution of fluids in a wellbore 130 using the downhole tool 140, as at 904. The fluids may include oil, gas, water, etc. In at least one embodiment, the nuclear magnetic resonance T2 distribution of the oil may be determined from the measured nuclear magnetic resonance T2 distribution of the fluids (which include oil, gas, water, etc.).

The method 900 may also include measuring a temperature while drilling (e.g., of the fluids) using the downhole tool 140, as at 906. The method 900 may also include measuring a pressure while drilling (e.g., of the fluids) using the downhole tool 140, as at 908. The method 900 may also include determining a viscosity of the fluid(s) from the nuclear magnetic resonance T2 distribution, the temperature, and the pressure, as at 910. In at least one embodiment, determining the viscosity of the fluid(s) may more specifically include determining the viscosity of the oil. The method 900 may also include varying a drilling parameter in response to the determined viscosity, as at 912. The drilling parameter may be any one of the drilling parameters described above.

Figure 10:
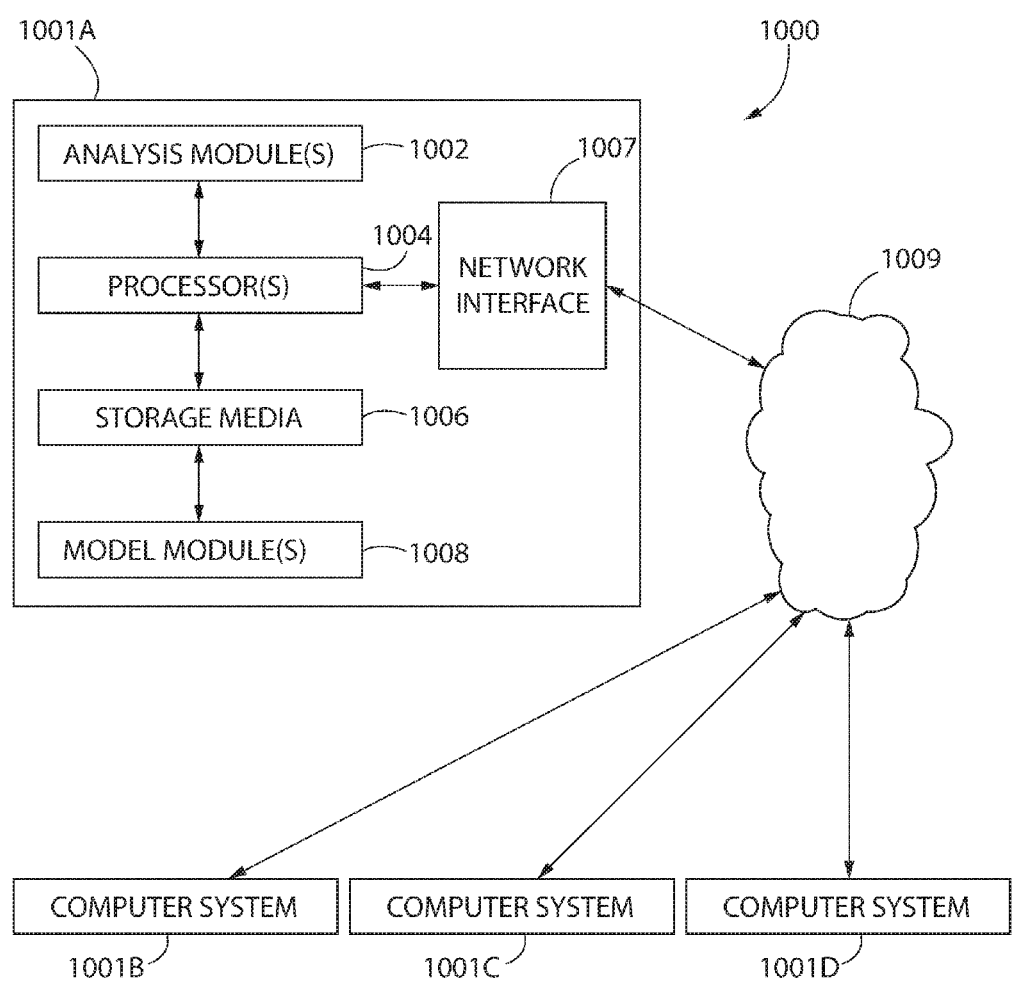
FIG. 10 illustrates a computing system for performing at least a portion of the method, according to an embodiment.

FIG. 10 illustrates a computing system for performing at least a portion of the method, according to an embodiment. In some embodiments, the methods of the present disclosure may be executed by a computing system. The computing system 1000 may include a computer or computer system 1001A, which may be an individual computer system 1001A or an arrangement of distributed computer systems. The computer system 1001A includes one or more analysis modules 1002 that are configured to perform various tasks according to some embodiments, such as one or more methods disclosed herein. To perform these various tasks, the analysis module 1002 executes independently, or in coordination with, one or more processors 1004, which is (or are) connected to one or more storage media 1006. The processor(s) 1004 is (or are) also connected to a network interface 1007 to allow the computer system 1001A to communicate over a data network 1009 with one or more additional computer systems and/or computing systems, such as 1001B, 1001C, and/or 1001D (note that computer systems 1001B, 1001C and/or 1001D may or may not share the same architecture as computer system 1001A, and may be located in different physical locations, e.g., computer systems 1001A and 1001B may be located in a processing facility, while in communication with one or more computer systems such as 1001C and/or 1001D that are located in one or more data centers, and/or located in varying countries on different continents).

A processor may include a microprocessor, microcontroller, processor module or subsystem, programmable integrated circuit, programmable gate array, or another control or computing device.

The storage media 1006 may be implemented as one or more computer-readable or machine-readable storage media. Note that while in the example embodiment of FIG. 10 storage media 1006 is depicted as within computer system 1001A, in some embodiments, storage media 1006 may be distributed within and/or across multiple internal and/or external enclosures of computing system 1001A and/or additional computing systems. Storage media 1006 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLURAY® disks, or other types of optical storage, or other types of storage devices. Note that the instructions discussed above may be provided on one computer-readable or machine-readable storage medium, or alternatively, may be provided on multiple computer-readable or machine-readable storage media distributed in a large system having possibly plural nodes. Such computer-readable or machine-readable storage medium or media is (are) considered to be part of an article (or article of manufacture). An article or article of manufacture may refer to any manufactured single component or multiple components. The storage medium or media may be located either in the machine running the machine-readable instructions, or located at a remote site from which machine-readable instructions may be downloaded over a network for execution.

In some embodiments, the computing system 1000 contains one or more model generation module(s) 1008. The model generation module(s) 1008 may be configured to generate one or more models of the formation properties based at least partially on the inverted petrophysical quantities of interest, as described in greater detail above.

It should be appreciated that computing system 1000 is only one example of a computing system, and that computing system 1000 may have more or fewer components than shown, may combine additional components not depicted in the example embodiment of FIG. 10, and/or computing system 1000 may have a different configuration or arrangement of the components depicted in FIG. 10. The various components shown in FIG. 10 may be implemented in hardware, software, or a combination of both hardware and software, including one or more signal processing and/or application specific integrated circuits.

Further, the processing methods described herein may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of protection of the invention.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. Moreover, the order in which the elements of the methods described herein are illustrate and described may be re-arranged, and/or two or more elements may occur simultaneously. The embodiments were chosen and described in order to best explain the principals of the invention and its practical applications, to thereby enable others skilled in the art to best utilize the invention and various embodiments with various modifications as are suited to the particular use contemplated.

While the claimed subject matter has been described with respect to a limited number of embodiments, those skilled in the art, having benefit of this disclosure, will appreciate that other embodiments can be devised which do not depart from the scope of the claimed subject matter as disclosed herein. Accordingly, the scope of the claimed subject matter should be limited only by the attached claims.

What is claimed is:

1. A method for generating a model of a formation property, comprising:
    acquiring formation property measurements that comprise different types of sensor measurements wherein acquiring the formation property measurements comprises acquiring the formation property measurements at a plurality of different times to form sets wherein each of the sets corresponds to one of the different times;
    generating the model of the formation property by deriving a set of bases for the sets that maximally correlates variates of the sets; and
    using the model to vary a drilling parameter.

2. The method of claim 1, wherein the formation property measurements are acquired downhole using a downhole tool.

3. The method of claim 1, further comprising:
    collecting a cutting downhole using a downhole tool; and
    analyzing the cutting at the surface to acquire at least a portion of the formation property measurements of at least one of the different types of measurements.

4. The method of claim 1, wherein the different types of sensor measurements comprise a resistivity measurement, a nuclear measurement, an acoustic measurement, a nuclear magnetic resonance measurement, or a combination thereof.

5. The method of claim 1, wherein the formation property comprises porosity, mineralogy, a fluid volume, or a combination thereof.

6. The method of claim 1, wherein the different types of sensor measurements comprise a density measurement, a neutron measurement, a nuclear magnetic resonance measurement, or a combination thereof, and wherein the model comprises a porosity model.

7. The method of claim 1, wherein the different types of sensor measurements comprise a nuclear magnetic resonance measurement, a gas to oil ratio, a pressure measurement, a temperature measurement, or a combination thereof, and wherein the model comprises a viscosity model.

8. The method of claim 1, wherein the drilling parameter comprises a weight on bit or a direction that a downhole tool is drilling.

9. The method of claim 1, wherein the acquired formation property measurements comprise at least one measurement that is contaminated by wellbore effects and invasion effects, and the wellbore effects and the invasion effects are not included in the model.

10. The method of claim 1, wherein acquiring the formation property measurements comprises measuring bulk density from nuclear radiation of a subterranean formation by gamma rays.

11. The method of claim 10, comprising inverting a petrophysical quantity as the formation property by inverting a porosity from the bulk density wherein the variates depend on the inverted porosity.

12. A computing system comprising:
    one or more processors; and
    a memory system comprising one or more non-transitory computer-readable media storing instructions that, when executed by at least one of the one or more processors, cause the computing system to perform operations, the operations comprising:
        acquiring formation property measurements that comprise different types of sensor measurements wherein acquiring the formation property measurements comprises acquiring the formation property measurements at a plurality of different times to form sets wherein each of the sets corresponds to one of the different times;

generating the model of the formation property by deriving a set of bases for the sets that maximally correlates variates of the sets; and using the model to vary a drilling parameter.

13. The method of claim 1 wherein generating the model generates a time-independent model of the formation property.

14. The method of claim 1 wherein the formation property is porosity.

15. The method of claim 1 wherein the formation property measurements at the plurality of different times comprise the formation property measurements at a common depth in a borehole wherein using the model to vary the drilling parameter varies further drilling of the borehole.

16. A method for generating a model of a formation property, comprising:

acquiring formation property measurements that comprise different types of sensor measurements wherein acquiring the formation property measurements comprises acquiring the formation property measurements at a plurality of different times to form sets wherein each of the sets corresponds to one of the different times; and generating the model of the formation property by deriving a set of bases for the sets that maximally correlates variates of the sets.

17. The method of claim 16 comprising using the model to output at least one value of the formation property.

18. The method of claim 16 comprising using the model to output values of the formation property over a length of a borehole.

19. The method of claim 16 comprising using the model to plot values of the formation property over a length of a borehole.

20. The method of claim 16 wherein one of the different times corresponds to a drill pass in a borehole and another one of the different times corresponds to a repeat pass in the borehole.

* * * * *